United States Patent
Shibasaki et al.

(10) Patent No.: US 9,901,913 B2
(45) Date of Patent: Feb. 27, 2018

(54) CATALYST AND METHOD FOR PRODUCING OPTICALLY ACTIVE ANTI-1,2-NITROALKANOL COMPOUND

(71) Applicant: Microbial Chemistry Research Foundation, Tokyo (JP)

(72) Inventors: Masakatsu Shibasaki, Tokyo (JP); Naoya Kumagai, Tokyo (JP); Takanori Ogawa, Tokyo (JP)

(73) Assignee: MICROBIAL CHEMISTRY RESEARCH FOUNDATION, Tokyo (JP)

( * ) Notice: Subject to any disclaimer, the term of this patent is extended or adjusted under 35 U.S.C. 154(b) by 0 days.

(21) Appl. No.: 14/767,620

(22) PCT Filed: Feb. 7, 2014

(86) PCT No.: PCT/JP2014/052859
§ 371 (c)(1),
(2) Date: Aug. 13, 2015

(87) PCT Pub. No.: WO2014/126008
PCT Pub. Date: Aug. 21, 2014

(65) Prior Publication Data
US 2015/0375219 A1 Dec. 31, 2015

(30) Foreign Application Priority Data
Feb. 14, 2013 (JP) .................................. 2013-026234

(51) Int. Cl.
*B01J 31/22* (2006.01)
*C07C 201/12* (2006.01)
*C07C 205/02* (2006.01)
*C07C 237/22* (2006.01)
*B01J 31/02* (2006.01)
*B01J 21/18* (2006.01)
*B01J 23/10* (2006.01)

(52) U.S. Cl.
CPC ............ *B01J 31/22* (2013.01); *B01J 21/185* (2013.01); *B01J 23/10* (2013.01); *B01J 31/0247* (2013.01); *B01J 31/0252* (2013.01); *B01J 31/0274* (2013.01); *B01J 31/0275* (2013.01); *B01J 31/2226* (2013.01); *C07C 201/12* (2013.01); *C07C 205/02* (2013.01); *C07C 237/22* (2013.01); *B01J 31/0212* (2013.01); *B01J 2231/30* (2013.01); *B01J 2231/342* (2013.01); *B01J 2531/0275* (2013.01); *B01J 2531/12* (2013.01); *B01J 2531/57* (2013.01); *B01J 2540/22* (2013.01); *C07B 2200/07* (2013.01)

(58) Field of Classification Search
None
See application file for complete search history.

(56) References Cited

U.S. PATENT DOCUMENTS 6,841,509 B1 * 1/2005 Hwang .................... B01J 21/18
423/447.5

FOREIGN PATENT DOCUMENTS

| CN | 1807380 | 7/2006 |
|---|---|---|
| DE | 102009011815 | 9/2010 |
| JP | 2005-089439 | 4/2005 |
| JP | 2010-189362 | 9/2010 |
| JP | 2010-189374 | 9/2010 |

OTHER PUBLICATIONS

Sureshkumar et al. ("A Modified Preparation Procedure for Carbon Nanotube-Confined Nd/Na Heterobimetallic Catalyst for anti-Selective Catalytic Asymmetric Nitroaldol Reactions", The Journal of Organic Chemistry, vol. 78, Issue 22, Oct. 2013, pp. 11494-11500).*
Serp et al. ("Catalysis in Carbon Nanotubes", ChemCatChem, vol. 2, Issue 1, available online Dec. 10, 2009, pp. 41-47).*
Smith, C.J. et al., Biphenyl-Substituted Oxazolidinones as Cholesteryl Ester Transfer Protein Inhibitors: Modifications of the Oxazolidinone Ring Leading to the Discovery of Anacetrapib, Journal of Medicinal Chemistry, vol. 54, 2011, pp. 4880-4895.
Uraguchi, D. et al., Chiral Tetraaminophosphonium Salt-Mediated Asymmetric Direct Henry Reaction, Journal of American Chemical Society, vol. 129, 2007, pp. 12392-12393.
Nitabaru, T. et al., Development of Anti-Selective Catalytic Asymmetric Nitroaldol Reaction with Heterogeneous Nd/Na Heterobimetallic Complex, 96$^{th}$ Symposium on Organic Synthesis, Japan, 2009, pp. 16-17, Table 2.
Morimoto, H. et al., A Broadly Applicable Copper Reagent for Trifluoromethylations and Perfluoroalkylations of Aryl Iodides and Bromides, Angew. Chem. Int. Ed., vol. 50, 2011, pp. 3793-3798.
Ouellet, S.G., et al., Preparative Scale Synthesis of the Biaryl Core of Anacetrapib via a Ruthenium-Catalyzed Direct Arylation Reaction: Unexpected Effect of Solvent Impurity on the Arylation Reaction, J. Org. Chem., vol. 76, 2011, pp. 1436-1439.
(Continued)

*Primary Examiner* — Rosalynd A Keys
(74) *Attorney, Agent, or Firm* — Carmody Torrance Sandak & Hennessey LLP

(57) ABSTRACT

A catalyst, which is obtained by mixing a compound expressed by the following Structural Formula (1), a nitroalkane compound, a neodymium-containing compound, a sodium-containing compound, and a carbon structure:

Structural Formula (1)

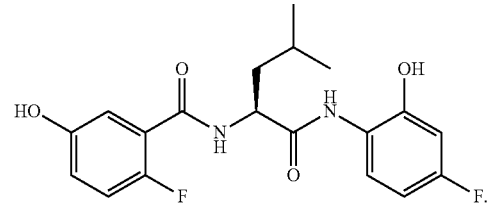

12 Claims, No Drawings

(56) References Cited

OTHER PUBLICATIONS

Gutstein, DE, et al., Anacetrapib, a Novel CETP Inhibitor: Pursuing a New Approach to Cardiovascular Risk Reduction, Clinical Pharmacology & Therapeutics, vol. 91, No. 1, Jan. 2012, pp. 109-122.
Ogawa, et al., "Self-Assembling Neodymium/Sodium Heterobimetallic Asymmetric Catalyst Confined in a Carbon Nanotube Network," Angewandte Chemie International Edition, vol. 52, No. 24, Jun. 10, 2013, pp. 6196-6201.
Sureshkumar, et al., "A Modified Preparation Procedure for Carbon Nanotube-Confined Nd/Na Heterobimetallic Catalyst for anti-Selective Catalytic Asymmetric Nitroaldol Reactions," Journal of Organic Chemistry, vol. 78, No. 22, Nov. 15, 2013, pp. 11494-11500.
Extended European Search Report dated Sep. 20, 2016 for the corresponding EP application (8 sheets).
Nitabaru, et al., "Anti-Selective Catalytic Asymmetric Nitroaldol Reaction via a Heterobimetallic Heterogeneous Catalyst," J. Am. Chem. Soc., vol. 131, pp. 13660-13869 (Sep. 9, 2009).
Xing, Liang, et al., "Simply Modified Chiral Disphosphine: Catalyst Recycling via Non-covalent Absorption on Carbon Nanotubes," Adv. Synth. Catal., vol. 350, pp. 1013-1016 (Mar. 18, 2008).
Chinese Office Action dated Sep. 20, 2016 issued for corresponding CN application with English translation.

\* cited by examiner

CATALYST AND METHOD FOR PRODUCING OPTICALLY ACTIVE ANTI-1,2-NITROALKANOL COMPOUND

TECHNICAL FIELD

The present invention relates to a novel catalyst useful in anti-selective catalytic asymmetric nitroaldol reaction, and a method for producing an optically active anti-1,2-nitroalkanol compound using the same.

BACKGROUND ART

Optically active anti-1,2-nitroalkanol compounds are useful as precursors of optically active anti-1,2-aminoalcohol compounds.

Optically active anti-1,2-aminoalcohol compounds are generally used as chiral building blocks having very high utility in organic synthetic chemistry, especially medicinal synthetic chemistry. For example, the optically active anti-1,2-aminoalcohol compounds are contained as basic units in pharmaceutical products such as β-agonist, many naturally-occurring biologically active compounds, and the like. Use of optically active anti-1,2-aminoalcohol compounds as starting materials or reaction reagents make it possible to efficiently and inexpensively produce compounds that can be used for the synthesis of various pharmaceuticals or naturally-occurring biologically active compounds.

Also, the optically active anti-1,2-nitroalkanol compounds themselves are useful as starting materials of pharmaceutical products.

For example, a compound expressed by the following Structural Formula (anacetrapib), which is regarded to be promising as a inhibitory drug for CETP (cholesteryl ester transfer protein), can be synthesized from optically active anti-1,2-nitroalkanol compounds (see, for example, NPL 1). Note that, in this proposed technique, a racemate of optically active anti-1,2-nitroalkanol compounds is used to obtain anacetrapib through optical resolution.

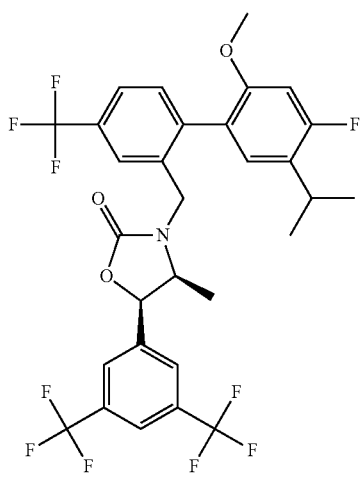 [SMILES: COc1cc(F)c(C(C)C)cc1-c1ccc(C(F)(F)F)cc1CN1C(=O)O[C@H](c2cc(C(F)(F)F)cc(C(F)(F)F)c2)[C@@H]1C]

One known method for anti-selectively producing the optically active anti-1,2-nitroalkanol compounds through catalytic asymmetric reaction is a method of allowing various aldehyde compounds and nitroalkane compounds to react in the presence of optically active tetraaminophosphonium salts (see, for example, NPL 2).

This method, however, has to be performed at an extremely low temperature of −78° C. and has a problem that it cannot be applied as an industrial production method.

In view of this, the present inventors proposed a method for anti-selectively producing optically active anti-1,2-nitroalkanol compounds through catalytic asymmetric reaction and a catalyst used in this reaction (see PTL 1).

In this proposed technique, nitroaldol reaction using various aldehyde compounds and nitroalkane compounds is performed using as a catalyst a heterogeneous composite metallic complex, in which lanthanoid such as neodymium is coordinated with an alkali metal such as sodium via a ligand of a specific amide compound. Use of it attains synthesis of optically active anti-1,2-nitroalkanol compounds with high anti-selectivity and very high enantiomeric excess. Also, the nitroaldol reaction rapidly proceeds even under cooling at about −40° C.

Since the above catalyst uses rare metals such as neodymium, it is desirable that it can be reused. At present, however, this catalyst in the above proposed technique cannot be reused.

Accordingly, at present, there is a demand to provide a catalyst that is capable of synthesizing an optically active anti-1,2-nitroalkanol compound with high anti-selectivity and very high enatiomeric excess and that is further reusable, and a method for producing an optically active anti-1,2-nitroalkanol compound using the catalyst.

CITATION LIST

Patent Literature

PTL 1: Japanese Patent Application Laid-Open (JP-A) No. 2010-189374

Non-Patent Literature

NPL 1: Cameron J. Smith, et al., J. Med. Chem., 2011, 54, 4880-4895

NPL 2: Uraguchi, D., et al., J. Am. Chem. Soc., 129, pp. 12392, 2007

SUMMARY OF INVENTION

Technical Problem

The present invention aims to solve the above existing problems and achieve the following object. That is, an object of the present invention is to provide a catalyst that is capable of synthesizing an optically active anti-1,2-nitroalkanol compound with high anti-selectivity and very high enatiomeric excess and that is further reusable, and a method for producing an optically active anti-1,2-nitroalkanol compound using the catalyst.

Solution to Problem

Means for solving the above problem are as follows.

A catalyst of the present invention is obtained by mixing a compound expressed by the following Structural Formula (1), a nitroalkane compound, a neodymium-containing compound, a sodium-containing compound, and a carbon structure.

Structural Formula (1)

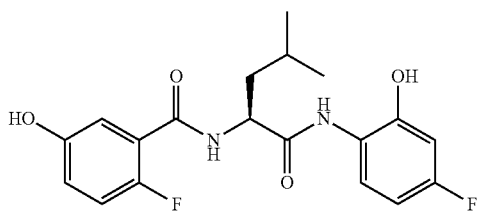

A method of the present invention for producing an optically active anti-1,2-nitroalkanol compound includes allowing an aldehyde compound and a nitroalkane compound having 2 or more carbon atoms to react in the presence of the above catalyst.

Advantageous Effects of Invention

The present invention can solve the above existing problems and achieve the above object, and can provide a catalyst that is capable of synthesizing an optically active anti-1,2-nitroalkanol compound with high anti-selectivity and very high enatiomeric excess and that is further reusable, and a method for producing an optically active anti-1,2-nitroalkanol compound using the catalyst.

DESCRIPTION OF EMBODIMENTS

Steric configurations in the chemical formulas and the general formulas described in the present specification and claims are absolute configurations unless otherwise specified.

Also, an "anti" configuration in the present specification and claims means that the hydroxyl group and the nitro group in 1,2-nitroalkanol compounds are in an anti configuration.

(Catalyst)

A catalyst of the present invention is obtained by mixing a compound expressed by the following Structural Formula (1), a nitroalkane compound, a neodymium-containing compound, a sodium-containing compound, and a carbon structure.

The catalyst is a heterogeneous composite metallic complex, in which the compound expressed by the Structural Formula (1) is coordinated with neodymium (Nd) and sodium (Na).

<Compound Expressed by Structural Formula (1)>

The catalyst contains a compound expressed by the following Structural Formula (1).

Structural Formula (1)

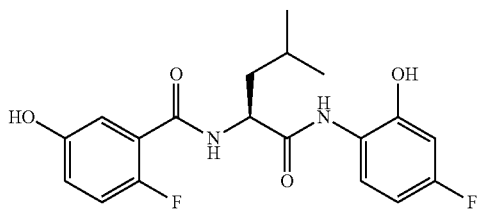

<Nitroalkane Compound>

The nitroalkane compound is not particularly limited and may be appropriately selected depending on the intended purpose.

The nitroalkane compound may have a substituent in an alkyl group constituting its main chain. Examples of the substituent include alkoxy groups, a carboxyl group, a hydroxyl group, and halogen atoms. The substituent may be protected with a protective group. The protective group is not particularly limited and may be appropriately selected depending on the intended purpose. Reference can be made to books such as Green, et al., Protective Groups in Organic Synthesis, 3rd Edition, 1999, John Wiley & Sons, Inc.

Also, the nitroalkane compound may contain any number of double bond(s) or triple bond(s) in the alkyl chain thereof.

The nitroalkane compound is preferably a compound represented by the following General Formula (1), more preferably nitroethane.

$$R^1\text{—}CH_2\text{—}NO_2 \qquad \text{General Formula (1)}$$

In the above General Formula (1), $R^1$ represents an alkyl group which has 1 to 20 carbon atoms and may have a substituent. Examples of the substituent include the above-listed substituents.

An amount of the nitroalkane compound relative to the compound expressed by the Structural Formula (1) in the preparation of the catalyst is not particularly limited and may be appropriately selected depending on the intended purpose. It is preferably 300 parts by mass to 1,000 parts by mass, more preferably 400 parts by mass to 500 parts by mass, relative to 100 parts by mass of the compound expressed by the Structural Formula (1).

<Neodymium-Containing Compound>

The neodymium-containing compound is not particularly limited and may be appropriately selected depending on the intended purpose so long as it contains neodymium (Nd) and when the catalyst is formed, it can provide neodymium with which the compound expressed by the Structural Formula (1) will coordinate. Examples thereof include $Nd_5O(OCH(CH_3)_2)_{13}$ and $NdO(OCH(CH_3)_2)_3$.

An amount of the neodymium-containing compound relative to the compound expressed by the Structural Formula (1) in the preparation of the catalyst is not particularly limited and may be appropriately selected depending on the intended purpose. It is preferably 0.2 mol to 1 mol, more preferably 0.4 mol to 0.6 mol, as an amount of neodymium relative to 1 mol of the compound expressed by the Structural Formula (1).

<Sodium-Containing Compound>

The sodium-containing compound is not particularly limited and may be appropriately selected depending on the intended purpose so long as it contains sodium (Na) and when the catalyst is formed, it can provide sodium with which the compound expressed by the Structural Formula (1) will coordinate. Examples thereof include sodium bis(trimethylsilyl)amide.

An amount of the sodium-containing compound relative to the compound expressed by the Structural Formula (1) in the preparation of the catalyst is not particularly limited and may be appropriately selected depending on the intended purpose. It is preferably 0.5 mol to 2 mol, more preferably 0.8 mol to 1.2 mol, as an amount of sodium relative to 1 mol of the compound expressed by the Structural Formula (1).

<Carbon Structure>

The carbon structure is not particularly limited and may be appropriately selected depending on the intended purpose so long as it is a structure formed of a six-membered network of carbon. Examples thereof include carbon nanotube, carbon nanohorn, and graphene. Among them, carbon nanotube is preferable.

The carbon nanotube may be a single-wall nanotube having a monolayer structure (SWNT) or a multi-wall nanotube having a multilayer structure (MWNT).

An average diameter and an average length of the carbon nanotube are not particularly limited and may be appropriately selected depending on the intended purpose.

The carbon structure may be a commercially available product. Examples of the commercially available product of the carbon nanotube include Baytubes (registered trademark) C70P and C150P (these products are of Bayer MaterialScience Co.).

An amount of the carbon structure relative to the compound expressed by the Structural Formula (1) in the preparation of the catalyst is not particularly limited and may be appropriately selected depending on the intended purpose. It is preferably 50 parts by mass to 400 parts by mass, more preferably 100 parts by mass to 200 parts by mass, relative to 100 parts by mass of the compound expressed by the Structural Formula (1). The amount falling within the above more preferable range is advantageous in that the resultant reaction yield will be high.

<Method for Preparing the Catalyst>

A method for preparing the catalyst is not particularly limited and may be appropriately selected depending on the intended purpose so long as it is a method of mixing the compound expressed by the Structural Formula (1), the nitroalkane compound, the neodymium-containing compound, the sodium-containing compound, and the carbon structure. Examples thereof include the following methods.

—Method A—

This method is a method including: treatment A1 of mixing the compound expressed by the Structural Formula (1), the neodymium-containing compound, the sodium-containing compound, and the carbon structure; and after the treatment A1, treatment A2 of further mixing the nitroalkane compound (hereinafter may be referred to as "Method A").

—Method B—

This method is a method including: treatment B1 of mixing the compound expressed by the Structural Formula (1), the neodymium-containing compound, the sodium-containing compound, and the nitroalkane compound; and after the treatment B1, treatment B2 of further mixing the carbon structure (hereinafter may be referred to as "Method B").

Among them, Method A is preferable since its reaction yield is superior.

One example of the Method A will be described.

First, the compound expressed by the Structural Formula (1), the neodymium-containing compound, and the sodium-containing compound are mixed in the presence of a solvent to obtain a white turbid suspension. Examples of the solvent include tetrahydrofuran.

Next, the carbon structure is added to the obtained suspension. Thereby, a state is established where the white turbid suspension and black precipitates (carbon structure) coexist.

Next, the nitroalkane compound is added thereto, followed by aging.

Thereby, the catalyst can be obtained.

In this method, the black catalyst, which is not white turbid, is obtained. It is believed that this is because the complex is uniformly dispersed in the carbon structure.

Next, one example of the Method B will be described.

First, the compound expressed by the Structural Formula (1), the neodymium-containing compound, and the sodium-containing compound are mixed in the presence of a solvent to obtain a white turbid suspension. Examples of the solvent include tetrahydrofuran.

Next, the nitroalkane compound is added to the obtained suspension. Thereby, its white turbidity disappears once and then appears again.

Next, the carbon structure is added thereto, followed by aging.

Thereby, the catalyst can be obtained.

In this method, the obtained catalyst is observed to have black color, which is derived from the carbon structure, and white turbidity.

Because white turbidity is observed, it is believed that the dispersion state of the complex in the carbon structure is poorer than that in the Method A.

Because the catalyst uses the carbon structure, the catalyst is easy to recover using a filter or the like. Also, even when the catalyst is recovered using a filter or the like after used for reaction, its catalytic activity will not considerably decrease. Therefore, the catalyst is easy to recover and reuse.

The catalyst can synthesize an optically active anti-1,2-nitroalkanol compound with high anti-selectivity and very high enantiomeric excess and further can be recovered and reused. Thus, the catalyst can be suitably used for the production of an optically active anti-1,2-nitroalkanol compound.

(Method for Producing Optically Active Anti-1,2-Nitroalkanol Compound)

A method of the present invention for producing an optically active anti-1,2-nitroalkanol compound includes allowing an aldehyde compound and a nitroalkane compound having 2 or more carbon atoms to react in the presence of the catalyst of the present invention.

<Aldehyde Compound>

The aldehyde compound is not particularly limited and may be appropriately selected depending on the intended purpose so long as it is a compound having an aldehyde group. Examples thereof include aromatic aldehyde compounds and aliphatic aldehyde compounds. The aliphatic group of the aliphatic aldehyde compound may have an aromatic ring.

The aldehyde compound may have a substituent. Examples of the substituent include alkoxy groups, a carboxyl group, a hydroxyl group, and halogen atoms. The substituent may be protected with a protective group. The protective group is not particularly limited and may be appropriately selected depending on the intended purpose. Reference can be made to books such as Green, et al., Protective Groups in Organic Synthesis, 3rd Edition, 1999, John Wiley & Sons, Inc.

Examples of the aromatic aldehyde compound include benzaldehyde, halogenobenzaldehyde, alkoxybenzaldehyde, alkylbenzaldehyde, and naphthylaldehyde.

Examples of the halogenobenzaldehyde include chlorobenzaldehyde, iodobenzaldehyde, and bromobenzaldehyde. Two or more halogen atoms may be substituted on the benzene ring thereof.

Examples of the alkoxybenzaldehyde include methoxybenzaldehyde and ethoxybenzaldehyde.

Examples of the alkylbenzaldehyde include methylbenzaldehyde and ethylbenzaldehyde.

Examples of the aliphatic aldehyde compound include alkylaldehyde and aralkylaldehyde.

Examples of the alkylaldehyde include butylaldehyde and cyclopropylaldehyde.

Examples of the aralkylaldehyde include 3-phenylpropanal, phenethylaldehyde, and benzylaldehyde.

<Nitroalkane Compound Having 2 or More Carbon Atoms>

The nitroalkane compound having 2 or more carbon atoms is not particularly limited and may be appropriately selected depending on the intended purpose.

The nitroalkane compound having 2 or more carbon atoms may have a substituent in an alkyl group constituting its main chain. Examples of the substituent include alkoxy groups, a carboxyl group, a hydroxyl group, and halogen atoms. The substituent may be protected with a protective group. The protective group is not particularly limited and may be appropriately selected depending on the intended purpose. Reference can be made to books such as Green, et al., Protective Groups in Organic Synthesis, 3rd Edition, 1999, John Wiley & Sons, Inc.

Also, the nitroalkane compound having 2 or more carbon atoms may contain any number of double bond(s) or triple bond(s) in the alkyl chain thereof.

The nitroalkane compound having 2 or more carbon atoms is preferably a compound represented by the following General Formula (2), more preferably nitroethane.

$$R^2-CH_2-NO_2 \qquad \text{General Formula (2)}$$

In the General Formula (2), $R^2$ represents an alkyl group which has 1 to 20 carbon atoms and may have a substituent. Examples of the substituent include the above-listed substituents.

The nitroalkane compound having 2 or more carbon atoms may be a compound identical to or different from the nitroalkane compound used in the preparation of the catalyst.

A ratio between the aldehyde compound and the nitroalkane compound having 2 or more carbon atoms in the above reaction is not particularly limited and may be appropriately selected depending on the intended purpose. An amount of the nitroalkane compound having 2 or more carbon atoms is preferably 2 mol to 20 mol, more preferably 3 mol to 10 mol, relative to 1 mol of the aldehyde compound.

An amount of the catalyst in the above reaction is not particularly limited and may be appropriately selected depending on the intended purpose. It is preferably 3 mol % to 20 mol %, more preferably 5 mol % to 10 mol %, as an amount of neodymium relative to 1 mol of the aldehyde compound. The amount falling within the above more preferable range is advantageous in that the amount of the catalyst and the reaction yield will be well balanced.

A time for the reaction is not particularly limited and may be appropriately selected depending on the intended purpose. It is preferably 1 hour to 80 hours, more preferably 10 hours 70 hours.

A temperature for the reaction is not particularly limited and may be appropriately selected depending on the intended purpose. It is preferably −70° C. to −30° C., more preferably −60° C. to −40° C.

EXAMPLES

The present invention will next be described in detail by way of Examples. The present invention, however, should not be construed as being limited to the Examples.

Note that, in the following Examples, "THF" denotes "tetrahydrofuran". "NaHMDS" denotes "sodium bis(trimethylsilyl)amide". "O$^i$Pr" denotes "isopropyloxy group". "DMF" denotes "N,N-dimethylformamide". "CNT" denotes "carbon nanotube". "Bn" denotes "benzyl group".

In the following Entries 1 to 8, a catalyst was synthesized and nitroaldol reaction presented in the following reaction scheme was performed.

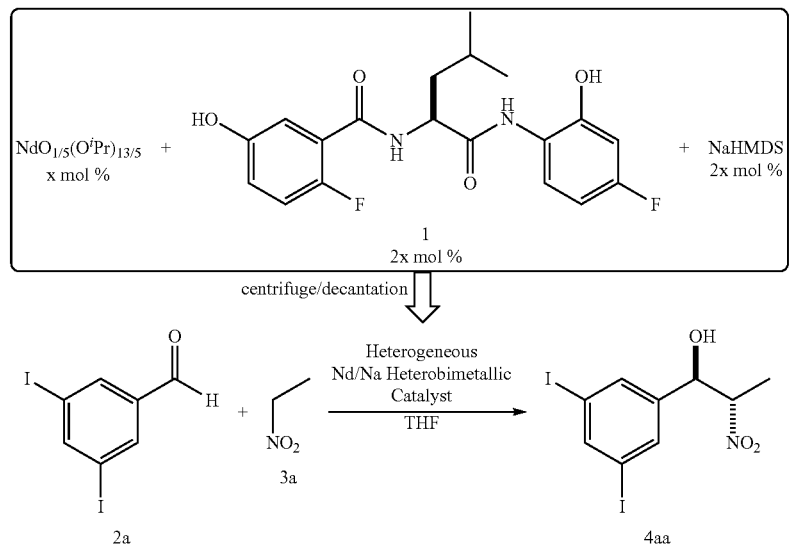

Synthesis Example 1

<Synthesis of Amide-Based Ligand 1>

A compound expressed by the following Structural Formula (1) (hereinafter may be referred to as "amide-based ligand 1") was synthesized in accordance with the method described in JP-A No. 2010-189374.

Structural Formula (1)

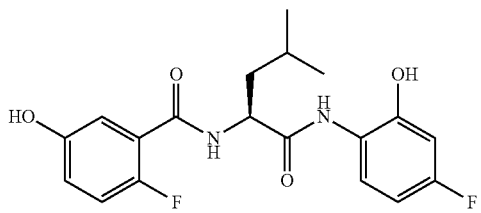

Experimental Example without Using CNT <Entry 1: Comparative Example>

A magnetic stirrer was added to a 20 mL evacuation test tube, which was dried in vacuum with heating. After the test tube had been left to cool, the amide-based ligand 1 (4.5 mg, 0.012 mmol) was added to the test tube, followed by drying in vacuum at room temperature for about 5 minutes. The test tube was purged with Ar gas, and then dry THF (0.3 mL) and $Nd_5O(O^iPr)_{13}$ (0.2 M in THF: 30 μL, 0.006 mmol, product of Kojundo Chemical Lab. Co., Ltd.) were sequentially added dropwise thereto at room temperature using a syringe. The obtained solution was cooled to 0° C., and then NaHMDS (1.0 M in THF: 12 μL, 0.012 mmol) was added dropwise thereto using a syringe. The resultant mixture was stirred at room temperature for 30 minutes to give a white suspension. The white suspension turned into a homogeneous solution by the dropwise addition of nitroethane (40 μL) at room temperature using a syringe. The homogeneous solution turned again into a white suspension when it continued to be stirred at room temperature. After stirring for 2 hours at room temperature, the white suspension was transferred to a 1.5 mL Eppendorf tube through pipetting. This tube was centrifuged at about 10,000 rpm for 5 seconds, and the supernatant was removed through decantation. Dry THF (1 mL) was added to the precipitated white catalyst remaining in the tube, and the mixture was suspended by stirring it for 30 seconds using a vortex mixer. Again, this tube was centrifuged at about 10,000 rpm for 5 seconds, and the supernatant was removed through decantation and the catalyst was washed. Similarly, dry THF (1 mL) was added thereto, and the mixture was stirred and suspended. Thereafter, the catalyst suspension was transferred to a 20 mL test tube, which had been dried in vacuum with heating, and placed in an Ar atmosphere. Dry THF (2 mL) and nitroethane (0.14 mL, 2.0 mmol) were added dropwise thereto using a syringe at room temperature, and the resultant mixture was placed in a thermostat bath set to a low temperature of −60° C. A dry THF solution (0.6 mL) of 3,5-diiodobenzaldehyde (72 mg, 0.2 mmol) was added dropwise thereto using a syringe for 1 minute, and the resultant mixture was stirred at −60° C. for 1 hour in an Ar atmosphere. A 0.2 M THF solution (0.3 mL) of acetic acid was added thereto, and the resultant mixture was stirred at −60° C. for 1 hour and then increased to room temperature. 1 N hydrochloric acid (1 mL) was added thereto and the resultant mixture was extracted with ethyl acetate. The organic layer was washed sequentially with a saturated aqueous sodium hydrogen carbonate solution and saturated brine, and dried with sodium sulfate anhydrate. After filtration and concentration, the residue was purified through silica gel column chromatography (hexane:ethyl acetate=10:1 to 5:1 (v/v)) to thereby obtain product 4aa as a pale yellow solid (85 mg, 98% yield).

Through high-performance liquid chromatography, the obtained product was determined to have an anti/syn ratio (98/2) and an enantiomeric excess (99% ee).

Column: Daicel CHIRALPAK AD-H, 0.46 cm in diameter×25 cm, UV detection wavelength: 254 nm, mobile phase: hexane/isopropanol=19/1 (v/v), flow rate: 1.0 mL/min, retention time: $t_R$=12.0 min (anti-4aa, minor), $t_R$=14.0 min (anti-4aa, major), $t_R$=15.1 min (syn-4aa, major), $_R$=44.1 min (syn-4aa, minor) (1R,2S)-1-(3,5-Diiodophenyl)-2-nitropropan-1-ol (Compound 4aa)

Pale Yellow Solid mp: 62° C.-63° C.

IR (KBr): v3487, 1547, 1390, 1365, 1276, 1182, 993, 706 $cm^{-1}$ $^1$H NMR ($CDCl_3$): δ8.02 (dd, J=1.6, 1.4 Hz, 1H), 7.70 (dd, J=1.6, 0.7 Hz, 2H), 5.35 (dd, J=3.2, 3.0 Hz, 1H), 4.63 (dq, J=6.9, 3.2 Hz, 1H), 2.78 (d, J=3.6 Hz, 1H), 1.49 (d, J=6.9 Hz, 3H).

$^{13}$C NMR ($CDCl_3$): δ145.2, 142.2, 134.3, 95.1, 86.8, 71.9, 11.7

ESI-MS m/z 432 [M−H]$^−$

HRMS (ESI-TOF) calcd. for $C_9H_9I_2NO_3Na$ m/z 455.8564 [M+Na]$^+$. found 455.8559.

$[α]D^{24}$-4.6 (c 1.00, $CHCl_3$, 99% ee)

HPLC (Daicel CHIRALPAK AD-H, 0.46 cm in diameter×25 cm, detection at 254 nm, n-hexane/iPrOH=19/1 (v/v), flow rate=1.0 mL/min) $t_R$=12.0 min (anti/minor), $t_R$=14.0 min (anti/major), $t_R$=15.1 min (syn/major), $t_R$=44.1 min (syn/minor).

Experimental Example of Method A Using CNT
<Entry 8: Example>

A magnetic stirrer was added to a 20 mL evacuation test tube, which was dried in vacuum with heating. After the test tube had been left to cool, the amide-based ligand 1 (9.0 mg, 0.024 mmol) was added to the test tube, followed by drying in vacuum at room temperature for about 5 minutes. The test tube was purged with Ar gas, and then dry THF (0.3 mL) and $Nd_5O(O^iPr)_{13}$ (0.2 M in THF: 60 μL, 0.012 mmol) were sequentially added dropwise thereto at room temperature using a syringe. The obtained solution was cooled to 0° C., and then NaHMDS (1.0 M in THF: 24 μL, 0.024 mmol) was added dropwise thereto using a syringe. The resultant mixture was stirred at room temperature for 30 minutes to give a white suspension. Thereafter, multi-wall carbon nanotube (Baytubes (registered trademark) C70P, 18 mg, product of Bayer MaterialScience Co.) was added to the white suspension. Subsequently, nitroethane (80 μL) was added dropwise thereto at room temperature using a syringe, followed by stirring at room temperature for 2 hours. Then, the black suspension was transferred to a 1.5 mL Eppendorf tube through pipetting while being washed with dry THF (1 mL). This tube was centrifuged at about 10,000 rpm for 5 seconds, and the supernatant was removed through decantation. Dry THF (1 mL) was added to the precipitated black catalyst remaining in the tube, and the mixture was suspended by stirring it for 30 seconds using a vortex mixer. Again, this tube was centrifuged at about 10,000 rpm for 5 seconds, and the supernatant was removed through decantation and the catalyst was washed. Similarly, dry THF (1 mL) was added thereto, and the mixture was stirred and suspended. Thereafter, the catalyst suspension was equally divided into six fractions, and one fraction containing Nd equivalent to 0.5 mol % (Nd: 0.002 mmol) was transferred to a 20 mL test tube, which had been dried in vacuum with heating, and placed in an Ar atmosphere. Dry THF (2.8 mL) and nitroethane (0.28 mL, 4.0 mmol) were added dropwise thereto using a syringe at room temperature, and the resultant mixture was placed in a thermostat bath set to a low temperature of −60° C. A dry THF solution (1 mL) of 3,5-diiodobenzaldehyde (143 mg, 0.4 mmol) was added dropwise thereto using a syringe for 1 minute, and the resultant mixture was stirred at −60° C. for 64 hours in an Ar atmosphere. A 0.2 M THF solution (0.3 mL) of acetic acid was added thereto, and the resultant mixture was stirred at −60° C. for 1 hour and then increased to room temperature. 1 N hydrochloric acid (1 mL) was added thereto and the resultant mixture was extracted with ethyl acetate. The organic layer was washed sequentially with a saturated aqueous sodium hydrogen carbonate solution and saturated brine, and dried with sodium sulfate anhydrate. After filtration and concentration, the residue was purified through silica gel column chromatography (hexane:ethyl acetate=10:1 to 5:1 (v/v)) to thereby obtain product 4aa (170 mg, 98% yield).

Through high-performance liquid chromatography, the obtained product was determined to have an anti/syn ratio (96/4) and an enantiomeric excess (95% ee).

Column: Daicel CHIRALPAKAD-H, 0.46 cm in diameter×25 cm, UV detection wavelength: 254 nm, mobile phase: hexane/isopropanol=19/1 (v/v), flow rate: 1.0 mL/min, retention time: $t_R$=12.0 min (anti-4aa, minor), $t_R$=14.0 min (anti-4aa, major), $t_R$=15.1 min (syn-4aa, major), R=44.1 min (syn-4aa, minor)

Experimental Example of Method B Using CNT
<Entry 6: Example>

A magnetic stirrer was added to a 20 mL evacuation test tube, which was dried in vacuum with heating. After the test tube had been left to cool, the amide-based ligand 1 (9.0 mg, 0.024 mmol) was added to the test tube, followed by drying in vacuum at room temperature for about 5 minutes. The test tube was purged with Ar gas, and then dry THF (0.3 mL) and $Nd_5O(O^iPr)_{13}$ (0.2 M in THF: 60 μL, 0.012 mmol) were sequentially added dropwise thereto at room temperature using a syringe. The obtained solution was cooled to 0° C., and then NaHMDS (1.0 M in THF: 24 μL, 0.024 mmol) was added dropwise thereto using a syringe. The resultant mixture was stirred at room temperature for 30 minutes to give a white suspension. The white suspension turned into a homogeneous solution by the dropwise addition of nitroethane (80 μL) at room temperature using a syringe. The homogeneous solution turned again into a white suspension when it continued to be stirred at room temperature. Multi-wall carbon nanotube (Baytubes (registered trademark) C70P, 9 mg, product of Bayer MaterialScience Co.) was added to this white suspension. After stirring for 2 hours at room temperature, the resultant mixture was transferred to a 1.5 mL Eppendorf tube through pipetting while being washed with dry THF (1 mL). This tube was centrifuged at about 10,000 rpm for 5 seconds, and the supernatant was removed through decantation. Dry THF (1 mL) was added to the precipitates remaining in the tube, and the mixture was suspended by stirring it for 30 seconds using a vortex mixer. Again, this tube was centrifuged at about 10,000 rpm for 5 seconds, and the supernatant was removed through decantation and the catalyst was washed. At this time, the white powder of the original catalyst and the black powder of the multi-wall carbon nanotube could be visually observed. Similarly, dry THF (1 mL) was added thereto, and the mixture was stirred and suspended. Thereafter, the catalyst suspension was equally divided into three fractions, and one fraction containing Nd equivalent to 1 mol % (Nd: 0.004 mmol) was transferred to a 20 mL test tube, which had been dried in vacuum with heating, and placed in an Ar atmosphere. Dry THF (2.7 mL) and nitroethane (0.28 mL, 4.0 mmol) were added dropwise thereto using a syringe at room temperature, and the resultant mixture was placed in a thermostat bath set to a low temperature of −60° C. A dry THF solution (1 mL) of 3,5-diiodobenzaldehyde (143 mg, 0.4 mmol) was added dropwise thereto using a syringe for 1 minute, and the resultant mixture was stirred at −60° C. for 22 hours in an Ar atmosphere. A 0.2 M THF solution (0.3 mL) of acetic acid was added thereto, and the resultant mixture was stirred at −60° C. for 1 hour and then increased to room temperature. 1 N hydrochloric acid (1 mL) was added thereto and the resultant mixture was extracted with ethyl acetate. The organic layer was washed sequentially with a saturated aqueous sodium hydrogen carbonate solution and saturated brine, and dried with sodium sulfate anhydrate. After filtration and concentration, the residue was purified through silica gel column chromatography (hexane: ethyl acetate=10:1 to 5:1 (v/v)) to thereby obtain product 4aa (55 mg, 32% yield).

Through high-performance liquid chromatography, the obtained product was determined to have an anti/syn ratio (94/6) and an enantiomeric excess (92% ee).

Column: Daicel CHIRALPAK AD-H, 0.46 cm in diameter×25 cm, UV detection wavelength: 254 nm, mobile phase: hexane/isopropanol=19/1 (v/v), flow rate: 1.0 mL/min, retention time: $t_R$=12.0 min (anti-4aa, minor), $t_R$=14.0 min (anti-4aa, major), $t_R$=15.1 min (syn-4aa, major), R=44.1 min (syn-4aa, minor)

Experimental Examples without Using CNT
<Entries 2 and 3; Comparative Examples>

Synthesis of a catalyst and nitroaldol reaction were performed in the same manner as in Entry 1 except that the catalyst amount and the reaction time were changed to those presented in Table 1. The results are presented in Table 1.

Experimental Examples Using CNT <Entries 4, 5 and 7; Examples>

Synthesis of a catalyst and nitroaldol reaction were performed in the same manner as in Entry 8 except that the kind of CNT, the amount of CNT, the catalyst amount, and the reaction time were changed to those presented in Table 1. The results are presented in Table 1.

Experimental Examples Using CNT <Entry 9: Example>

The following reaction was performed.

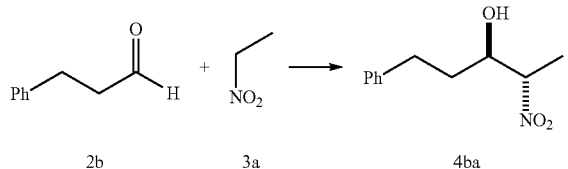

A magnetic stirrer was added to a 20 mL evacuation test tube, which was dried in vacuum with heating. After the test tube had been left to cool, the amide-based ligand 1 (9.0 mg, 0.024 mmol) was added to the test tube, followed by drying in vacuum at room temperature for about 5 minutes. The test tube was purged with Ar gas, and then dry THF (0.3 mL) and Nd$_5$O(O$^i$pr)$_{13}$ (0.2 M in THF: 60 L, 0.012 mmol) were sequentially added dropwise thereto at room temperature using a syringe. The obtained solution was cooled to 0° C., and then NaHMDS (1.0 M in THF: 24 µL, 0.024 mmol) was added dropwise thereto using a syringe. The resultant mixture was stirred at room temperature for 30 minutes to give a white suspension. Thereafter, multi-wall carbon nanotube (Baytubes (registered trademark) C70P, 18 mg, product of Bayer MaterialScience Co.) was added to the white suspension. Subsequently, nitroethane (80 µL) was added dropwise thereto at room temperature using a syringe, followed by stirring at room temperature for 2 hours. Then, the black suspension was transferred to a 1.5 mL Eppendorf tube through pipetting while being washed with dry THF (1 mL). This tube was centrifuged at about 10,000 rpm for 5 seconds, and the supernatant was removed through decantation. Dry THF (1 mL) was added to the precipitated black catalyst remaining in the tube, and the mixture was suspended by stirring it for 30 seconds using a vortex mixer. Again, this tube was centrifuged at about 10,000 rpm for 5 seconds, and the supernatant was removed through decantation and the catalyst was washed. Similarly, dry THF (1 mL) was added thereto, and the mixture was stirred and suspended. Thereafter, the catalyst suspension was equally divided into three fractions, and one fraction containing Nd equivalent to 1 mol % (Nd: 0.004 mmol) was transferred to a 20 mL test tube, which had been dried in vacuum with heating, and placed in an Ar atmosphere. Dry THF (2.7 mL) and nitroethane (0.28 mL, 4.0 mmol, Compound 3a) were added dropwise thereto using a syringe at room temperature, and the resultant mixture was placed in a thermostat bath set to a low temperature of −40° C. A dry THF solution (1 mL) of 3-phenylpropanal (54 mg, 0.4 mmol, Compound 2b) was added dropwise thereto using a syringe for 1 minute, and the resultant mixture was stirred at −40° C. for 40 hours in an Ar atmosphere. A 0.2 M THF solution (0.3 mL) of acetic acid was added thereto, and the resultant mixture was stirred at −40° C. for 1 hour and then increased to room temperature. 1 N hydrochloric acid (1 mL) was added thereto and the resultant mixture was extracted with ethyl acetate. The organic layer was washed sequentially with a saturated aqueous sodium hydrogen carbonate solution and saturated brine, and dried with sodium sulfate anhydrate. After filtration and concentration, the residue was purified through silica gel column chromatography (hexane:ethyl acetate=10:1 to 5:1 (v/v)) to thereby obtain product 4ba (72 mg, 86% yield).

Through high-performance liquid chromatography, the obtained product was determined to have an anti/syn ratio (81/19) and an enantiomeric excess (81% ee).

Column: Daicel CHIRALPAKAD-H, 0.46 cm in diameter×25 cm, UV detection wavelength: 254 nm, mobile phase: hexane/isopropanol=9/1 (v/v), flow rate: 1.0 mL/min, retention time: t$_R$=8.6 min (anti-4ba, minor), t$_R$=9.0 min (anti-4ba, major)

It was confirmed that this product was a compound known in a document, and was the above target compound by comparing its spectral data with those described in the document.

Experimental Examples Using CNT <Entry 10: Example>

The following reaction was performed.

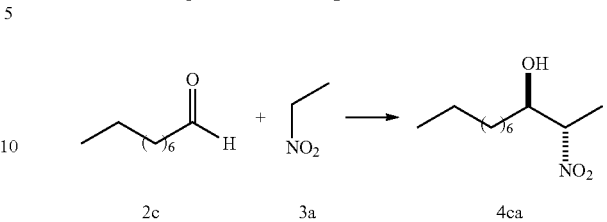

2c     3a     4ca

A magnetic stirrer was added to a 20 mL evacuation test tube, which was dried in vacuum with heating. After the test tube had been left to cool, the amide-based ligand 1 (9.0 mg, 0.024 mmol) was added to the test tube, followed by drying in vacuum at room temperature for about 5 minutes. The test tube was purged with Ar gas, and then dry THF (0.3 mL) and Nd$_5$O(O$^i$Pr)$_{13}$ (0.2 M in THF: 60 µL, 0.012 mmol) were sequentially added dropwise thereto at room temperature using a syringe. The obtained solution was cooled to 0° C., and then NaHMDS (1.0 M in THF: 24 µL, 0.024 mmol) was added dropwise thereto using a syringe. The resultant mixture was stirred at room temperature for 30 minutes to give a white suspension. The white suspension turned into a homogeneous solution by the dropwise addition of nitroethane (80 µL) at room temperature using a syringe. The homogeneous solution turned again into a white suspension when it continued to be stirred at room temperature. Multi-wall carbon nanotube (Baytubes (registered trademark) C70P, 9 mg, product of Bayer MaterialScience Co.) was added to this white suspension. After stirring at room temperature for 2 hours, the resultant mixture was transferred to a 1.5 mL Eppendorf tube through pipetting while being washed with dry THF (1 mL). This tube was centrifuged at about 10,000 rpm for 5 seconds, and the supernatant was removed through decantation. Dry THF (1 mL) was added to the precipitates remaining in the tube, and the mixture was suspended by stirring it for 30 seconds using a vortex mixer. Again, this tube was centrifuged at about 10,000 rpm for 5 seconds, and the supernatant was removed through decantation and the catalyst was washed. At this time, the white powder of the original catalyst and the black powder of the multi-wall carbon nanotube could be visually observed. Similarly, dry THF (1 mL) was added thereto, and the mixture was stirred and suspended. Thereafter, the catalyst suspension was equally divided into three fractions, and one fraction containing Nd equivalent to 1 mol % (Nd: 0.004 mmol) was transferred to a 20 mL test tube, which had been dried in vacuum with heating, and placed in an Ar atmosphere. Dry THF (2.7 mL) and nitroethane (0.28 mL, 4.0 mmol, Compound 3a) were added dropwise thereto using a syringe at room temperature, and the resultant mixture was placed in a thermostat bath set to a low temperature of −40° C. A dry THF solution (1 mL) of nonanal (143 mg, 0.4 mmol, Compound 2c) was added dropwise thereto using a syringe for 1 minute, and the resultant mixture was stirred at −40° C. for 40 hours in an Ar atmosphere. A 0.2 M THF solution (0.3 mL) of acetic acid was added thereto, and the resultant mixture was stirred at −40° C. for 1 hour and then increased to room temperature. 1 N hydrochloric acid (1 mL) was added thereto and the resultant mixture was extracted with ethyl acetate. The organic layer was washed sequentially with a saturated aqueous sodium hydrogen carbonate solution and saturated brine, and dried with sodium sulfate anhydrate. After filtration and concentration, the residue was purified through silica gel column chromatography (hexane:ethyl acetate=10:1 to 5:1 (v/v)) to thereby obtain product 4ca (69 mg, 79% yield).

Through high-performance liquid chromatography, the obtained product was determined to have an anti/syn ratio (80/20) and an enantiomeric excess (88% ee).

Column: Daicel CHIRALPAK AD-H, 0.46 cm in diameter×25 cm, UV detection wavelength: 210 nm, mobile phase: hexane/isopropanol=99/1 (v/v), flow rate: 0.5 mL/min, retention time: $t_R$=47.3 min (anti-4ca, minor), $t_R$=49.3 min (anti-4ca, major)

It was confirmed that this product was a compound known in a document, and was the above target compound by comparing its spectral data with those described in the document.

Experimental Examples Using CNT <Entry 11: Example>

The following reaction was performed.

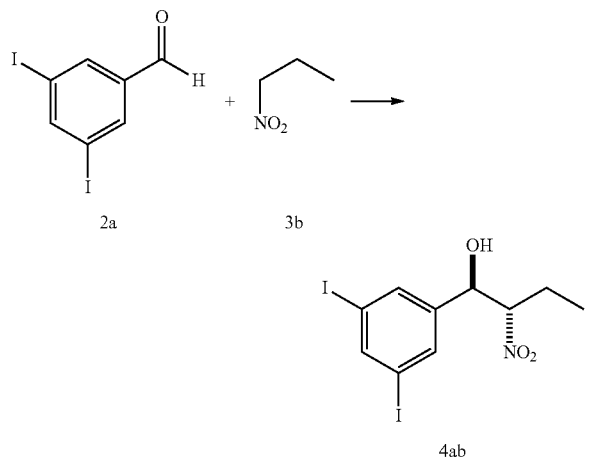

A magnetic stirrer was added to a 20 mL evacuation test tube, which was dried in vacuum with heating. After the test tube had been left to cool, the amide-based ligand 1 (9.0 mg, 0.024 mmol) was added to the test tube, followed by drying in vacuum at room temperature for about 5 minutes. The test tube was purged with Ar gas, and then dry THF (0.3 mL) and $Nd_5O(O^iPr)_{13}$ (0.2 M in THF: 60 µL, 0.012 mmol) were sequentially added dropwise thereto at room temperature using a syringe. The obtained solution was cooled to 0° C., and then NaHMDS (1.0 M in THF: 24 µL, 0.024 mmol) was added dropwise thereto using a syringe. The resultant mixture was stirred at room temperature for 30 minutes to give a white suspension. The white suspension turned into a homogeneous solution by the dropwise addition of nitroethane (80 µL) at room temperature using a syringe. The homogeneous solution turned again into a white suspension when it continued to be stirred at room temperature. Multi-wall carbon nanotube (Baytubes (registered trademark) C70P, 9 mg, product of Bayer MaterialScience Co.) was added to this white suspension. After stirring at room temperature for 2 hours, the resultant mixture was transferred to a 1.5 mL Eppendorf tube through pipetting while being washed with dry THF (1 mL). This tube was centrifuged at about 10,000 rpm for 5 seconds, and the supernatant was removed through decantation. Dry THF (1 mL) was added to the precipitates remaining in the tube, and the mixture was suspended by stirring it for 30 seconds using a vortex mixer. Again, this tube was centrifuged at about 10,000 rpm for 5 seconds, and the supernatant was removed through decantation and the catalyst was washed. At this time, the white powder of the original catalyst and the black powder of the multi-wall carbon nanotube could be visually observed. Similarly, dry THF (1 mL) was added thereto, and the mixture was stirred and suspended. Thereafter, the catalyst suspension was equally divided into three fractions, and one fraction containing Nd equivalent to 1 mol % (Nd: 0.004 mmol) was transferred to a 20 mL test tube, which had been dried in vacuum with heating, and placed in an Ar atmosphere. Dry THF (2.7 mL) and nitropropane (0.28 mL, 4.0 mmol, Compound 3b) were added dropwise thereto using a syringe at room temperature, and the resultant mixture was placed in a thermostat bath set to a low temperature of −60° C. A dry THF solution (1 mL) of 3,5-diiodobenzaldehyde (143 mg, 0.4 mmol, Compound 2a) was added dropwise thereto using a syringe for 1 minute, and the resultant mixture was stirred at −60° C. for 20 hours in an Ar atmosphere. A 0.2 M THF solution (0.3 mL) of acetic acid was added thereto, and the resultant mixture was stirred at −60° C. for 1 hour and then increased to room temperature. 1 N hydrochloric acid (1 mL) was added thereto and the resultant mixture was extracted with ethyl acetate. The organic layer was washed sequentially with a saturated aqueous sodium hydrogen carbonate solution and saturated brine, and dried with sodium sulfate anhydrate. After filtration and concentration, the residue was purified through silica gel column chromatography (hexane:ethyl acetate=10:1 to 5:1 (v/v)), to thereby obtain product 4ab (167 mg, 94% yield).

Through high-performance liquid chromatography, the obtained product was determined to have an anti/syn ratio (86/14) and an enantiomeric excess (93% ee).

Column: Daicel CHIRALPAK AD-H, 0.46 cm in diameter×25 cm, UV detection wavelength: 254 nm, mobile phase: hexane/isopropanol=19/1 (v/v), flow rate: 1.0 mL/min, retention time: $t_R$=11.1 min (anti-4ab, minor), $t_R$=12.3 min (anti-4ab, major)

(Compound 4ab)

Colorless Oil

IR (neat): ν3521, 1539, 1374, 1297, 1189 $cm^{-1}$ $^1$H NMR ($CDCl_3$): δ8.02 (s, 1H), 7.69 (s, 2H), 5.12-5.11 (m, 1H), 4.94-4.90 (m, 1H), 2.83-2.80 (m, 1H), 2.21-2.09 (m, 2H), 1.85-1.74 (m, 2H), 0.95 (t, J=7.6 Hz, 3H)

$^{13}$C NMR ($CDCl_3$): δ145.4, 142.3, 134.5, 95.0, 94.0, 72.4, 20.8, 10.3

ESI-MS m/z 446 [M−H]$^-$

HRMS (ESI-TOF) calcd. for $C_{10}H_{11}I_2NO_3Na$ m/z 469.8721 [M+Na]$^+$. found 469.8714.

[α]$D^{24}$ 7.7 (c 1.48, $CHCl_3$, 93% ee)

Experimental Examples Using CNT Entry 12: Example>

The following reaction was performed.

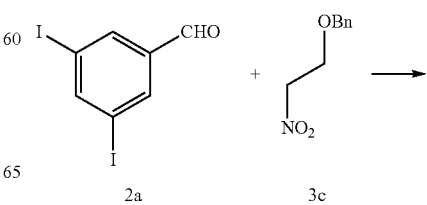

-continued

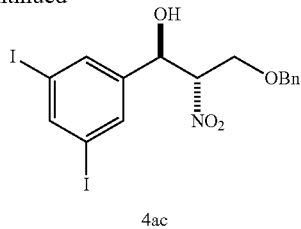

4ac

A magnetic stirrer was added to a 20 mL evacuation test tube, which was dried in vacuum with heating. After the test tube had been left to cool, the amide-based ligand 1 (9.0 mg, 0.024 mmol) was added to the test tube, followed by drying in vacuum at room temperature for about 5 minutes. The test tube was purged with Ar gas, and then dry THF (0.3 mL) and $Nd_5O(O^iPr)_3$ (0.2 M in THF: 60 μL, 0.012 mmol) were sequentially added dropwise thereto at room temperature using a syringe. The obtained solution was cooled to 0° C., and then NaHMDS (1.0 M in THF: 24 μL, 0.024 mmol) was added dropwise thereto using a syringe. The resultant mixture was stirred at room temperature for 30 minutes to give a white suspension. The white suspension turned into a homogeneous solution by the dropwise addition of nitroethane (80 μL) at room temperature using a syringe. The homogeneous solution turned again into a white suspension when it continued to be stirred at room temperature. Multi-wall carbon nanotube (Baytubes (registered trademark) C70P, 9 mg, product of Bayer MaterialScience Co.) was added to this white suspension. After stirring at room temperature for 2 hours, the resultant mixture was transferred to a 1.5 mL Eppendorf tube through pipetting while being washed with dry THF (1 mL). This tube was centrifuged at about 10,000 rpm for 5 seconds, and the supernatant was removed through decantation. Dry THF (1 mL) was added to the precipitates remaining in the tube, and the mixture was suspended by stirring it for 30 seconds using a vortex mixer. Again, this tube was centrifuged at about 10,000 rpm for 5 seconds, and the supernatant was removed through decantation and the catalyst was washed. At this time, the white powder of the original catalyst and the black powder of the multi-wall carbon nanotube could be visually observed. Similarly, dry THF (1 mL) was added thereto, and the mixture was stirred and suspended. Thereafter, the catalyst suspension was equally divided into three fractions, and one fraction containing Nd equivalent to 1 mol % (Nd: 0.004 mmol) was transferred to a 20 mL test tube, which had been dried in vacuum with heating, and placed in an Ar atmosphere. Dry THF (1.7 mL) and dry THF solution (1 mL) of ((2-nitroethoxy)methyl)benzene (362 mg, 2.0 mmol, Compound 3c) were added dropwise thereto using a syringe at room temperature, and the resultant mixture was placed in a thermostat bath set to a low temperature of −60° C. A dry THF solution (1 mL) of 3,5-diiodobenzaldehyde (143 mg, 0.4 mmol, Compound 2a) was added dropwise thereto using a syringe for 1 minute, and the resultant mixture was stirred at −60° C. for 40 hours in an Ar atmosphere. A 0.2 M THF solution (0.3 mL) of acetic acid was added thereto, and the resultant mixture was stirred at −60° C. for 1 hour and then increased to room temperature. 1 N hydrochloric acid (1 mL) was added thereto and the resultant mixture was extracted with ethyl acetate. The organic layer was washed sequentially with a saturated aqueous sodium hydrogen carbonate solution and saturated brine, and dried with sodium sulfate anhydrate. After filtration and concentration, the residue was purified through silica gel column chromatography (hexane:dichloromethane=1:1 to 1:2 (v/v)) to thereby obtain product 4ac (155 mg, 72% yield).

Through high-performance liquid chromatography, the obtained product was determined to have an anti/syn ratio (83/17) and an enantiomeric excess (89% ee).

Column: Daicel CHIRALPAK AD-H, 0.46 cm in diameter×25 cm (two columns connected), UV detection wavelength: 254 nm, mobile phase: hexane/isopropanol=9/1 (v/v), flow rate: 1.0 mL/min, retention time: $t_R$=20.7 min (anti-4ac, minor), $t_R$=23.0 min (anti-4ac, major)

(Compound 4ac)

Colorless Oil

IR (neat): ν3537, 1546, 1370, 1191 $cm^{-1}$ $^1$H NMR (CDCl$_3$): δ8.02 (s, 1H), 7.67 (s, 2H), 7.38-7.23 (m, 5H), 5.29-5.27 (m, 1H), 4.77-4.73 (m, 1H), 4.58-4.54 (m, 1H), 4.49 (d, J=11.7 Hz, 1H), 4.04 (dd, J=11.0, 7.3 Hz, 1H), 3.91 (dd, J=11.2, 3.2 Hz, 1H)

ESI-MS m/z 562 [M+Na]$^+$

HRMS (ESI-TOF) calcd. for $C_{16}H_{15}I_2NO_4Na$ m/z 561.8983 [M+Na]$^+$. found 561.8968.

TABLE 1

| Entry | aldehyde | nitro alkane | CNT (mass % to 1) | prepn. Method | x (mol %) | Temp. (° C.) | Time (h) | Yield (%) | anti/syn | ee(%) (anti) |
|---|---|---|---|---|---|---|---|---|---|---|
| 1 | 2a | 3a | — | — | 3 | −60 | 1 | 98 | 98/2 | 99 |
| 2 | 2a | 3a | — | — | 1 | −60 | 4 | 8 | 97/3 | 98 |
| 3 | 2a | 3a | — | — | 1 | −60 | 20 | 24 | 98/2 | 98 |
| 4 | 2a | 3a | C70P | 100 | A | 1 | −60 | 20 | 99 | 98/2 | 99 |
| 5 | 2a | 3a | C150P | 100 | A | 1 | −60 | 20 | 95 | 98/2 | 99 |
| 6 | 2a | 3a | C70P | 100 | B | 1 | −60 | 22 | 32 | 94/6 | 92 |
| 7 | 2a | 3a | C70P | 100 | A | 0.5 | −60 | 64 | 87 | 96/4 | 95 |
| 8 | 2a | 3a | C70P | 200 | A | 0.5 | −60 | 64 | 98 | 96/4 | 95 |
| 9 | 2b | 3a | C70P | 200 | A | 1 | −40 | 40 | 86 | 81/19 | 81 |
| 10 | 2c | 3a | C70P | 200 | A | 1 | −40 | 40 | 79 | 80/20 | 88 |
| 11 | 2a | 3b | C70P | 200 | A | 1 | −60 | 20 | 94 | 86/14 | 93 |
| 12 | 2a | 3c | C70P | 200 | A | 1 | −60 | 40 | 97 | 56/44 | 75 |

In Table 1, "X" corresponds to the "X" in the above reaction scheme and denotes an amount (mol %) of a catalyst starting material relative to 1 mol of the aldehyde compound.

The amount of CNT presented is relative to the amide-based ligand 1.

"C70P" denotes Baytubes (registered trademark) C70P (product of Bayer MaterialScience Co.).

"C150P" denotes Baytubes (registered trademark) C150P (product of Bayer MaterialScience Co.).

Experiment on Recovery and Reuse of Catalyst: Example

<Operation of Entry 101>

A magnetic stirrer was added to a 20 mL evacuation test tube, which was dried in vacuum with heating. After the test tube had been left to cool, the amide-based ligand 1 (9 mg, 0.024 mmol, 6 mol %) was added to the test tube, followed by drying in vacuum at room temperature for about 5 minutes. The test tube was purged with Ar gas, and then dry THF (0.3 mL) and $Nd_5O(O^iPr)_{13}$ (0.2 M in THF: 60 µL, 0.012 mmol, 3 mol %) were sequentially added dropwise thereto at room temperature using a syringe. The obtained solution was cooled to 0° C., and then NaHMDS (1.0 M in THF: 24 µL, 0.024 mmol, 6 mol %) was added dropwise thereto using a syringe. The resultant mixture was stirred at room temperature for 30 minutes, and then multi-wall carbon nanotube (Baytubes (registered trademark) C70P, 9 mg, product of Bayer MaterialScience Co.) was added to the white suspension. Subsequently, nitroethane (80 µL) was added dropwise thereto at room temperature using a syringe, followed by stirring at room temperature for 2 hours. Then, the resultant mixture was transferred to a 1.5 mL Eppendorf tube through pipetting while being washed with dry THF (1 mL). This tube was centrifuged at about 10,000 rpm for 5 seconds, and the supernatant was removed through decantation. Dry THF (1 mL) was added to the precipitated black catalyst in the tube, and the mixture was suspended by stirring it for 30 seconds using a vortex mixer. Again, this tube was centrifuged at about 10,000 rpm for 5 seconds, and the supernatant was removed through decantation and the catalyst was washed. Similarly, dry THF (1 mL) was added thereto, and the mixture was stirred and suspended. Thereafter, the catalyst suspension was transferred to a 20 mL test tube with a glass filter (product of TOKYO RIKAKIKAI CO., LTD.), which had been dried in vacuum, and placed in an Ar atmosphere. Dry THF (2 mL) and nitroethane (0.28 mL, 4.0 mmol) were added dropwise thereto using a syringe at room temperature, and the resultant mixture was placed in a thermostat bath set to a low temperature of −60° C. A dry THF solution (1 mL) of 3,5-diiodobenzaldehyde (143 mg, 0.4 mmol) was added dropwise thereto using a syringe for 1 minute, and the resultant mixture was allowed to react at −60° C. for 1 hour in an Ar atmosphere under vibration at about 240 rpm. After confirming the completion of the reaction through thin-layer chromatography, the cap at the bottom of the test tube was replaced with a syringe. The reaction mixture was filtered by the pressure applied from an Ar balloon at −60° C., and added dropwise to a 0.2 M THF solution (2 mL) of acetic acid. Dry THF (1 mL) was added to the reaction container, followed by filtration similarly, to thereby wash the catalyst. 1 N hydrochloric acid (1 mL) was added thereto and the resultant mixture was extracted with ethyl acetate. The organic layer was washed sequentially with a saturated aqueous sodium hydrogen carbonate solution and saturated brine, and dried with sodium sulfate anhydrate. After filtration and concentration, the residue was purified through silica gel column chromatography (hexane:ethyl acetate=10:1 to 5:1 (v/v)) to thereby obtain product 4aa (162 mg, 94% yield).

Through high-performance liquid chromatography, the obtained product was determined to have an anti/syn ratio (98/2) and an enantiomeric excess (99% ee).

Column: Daicel CHIRALPAK AD-H, 0.46 cm in diameter×25 cm, UV detection wavelength: 254 nm, mobile phase: hexane/isopropanol=19/1 (v/v), flow rate: 1.0 mL/min, retention time: $t_R$=12.0 min (anti-4aa, minor), $t_R$=14.0 min (anti-4aa, major), $t_R$=15.1 min (syn-4aa, major), $t_R$=45.7 min (syn-4aa, minor)

<Operation of Entry 102>

The syringe at the bottom of the reaction container was replaced again with the cap, and dry THF (3 mL) and nitroethane (0.28 mL, 4.0 mmol) were added dropwise at room temperature to the catalyst in the reaction container using a syringe. The catalyst suspension was placed in a thermostat bath set to a low temperature of −60° C. A dry THF solution (1 mL) of 3,5-diiodobenzaldehyde (143 mg, 0.4 mmol) was added dropwise thereto using a syringe for 1 minute, and the resultant mixture was allowed to initiate the second reaction at −60° C. in an Ar atmosphere under vibration at about 240 rpm (operation of Entry 102). The results are presented in Table 2.

<Operation of Entries 103 to 106>

The reaction product was recovered and the catalyst was reused in the same manner as in Entry 102 except that the reaction time was changed to each of those presented in Table 2. The results are presented in Table 2.

TABLE 2

| Entry | Temp. (° C.) | Time (h) | Yield (%) | anti/syn | ee(%) (anti) | comment |
|---|---|---|---|---|---|---|
| 101 | −60 | 1 | 94 | 98/2 | 99 | 1st run |
| 102 | −60 | 1 | 96 | 99/1 | 99 | 2nd run |
| 103 | −60 | 3 | 90 | 99/1 | 99 | 3rd run |
| 104 | −60 | 3 | 97 | 99/1 | 98 | 4th run |
| 105 | −60 | 5 | 53 | 98/2 | 98 | 5th run |
| 106 | −60 | 14 | 114 | 98/2 | 98 | 6th run |

Note in Table 2 that, the yield denotes an isolation yield, and the anti/syn ratio was measured through chiral HPLC (high-performance liquid chromatography).

It was confirmed that the catalyst could be reused six times.

Note that, the yield decreased at the 5th run and exceeded 100% at the 6th run, and this is likely because clogging of the filter occurred upon filtration of the catalyst and insufficient washing resulted in the decrease in the yield at the 5th run, and the residual product was contained upon recovery of the reaction liquid at the 6th run.

Experiment on Recovery and Reuse of Catalyst without Using CNT: Comparative Example In the reaction of Entry 1, the reaction was performed using a 20 mL test tube with a glass filter, and after the reaction, the glass filter was used to try separating the catalyst from the reaction product. However, because the catalyst was very fine particles, there was a difficulty in separating it, and the catalyst could not be recovered and reused.

Also, the catalyst of Entry 1 was inferior in stability to air to the catalysts of Entries 4 to 12, which is another reason why it could not be recovered and reused.

(Synthesis of Anacetrapib)

In accordance with the following reaction scheme, anacetrapib was synthesized from Compound 4aa.

Synthesis of Compound 5

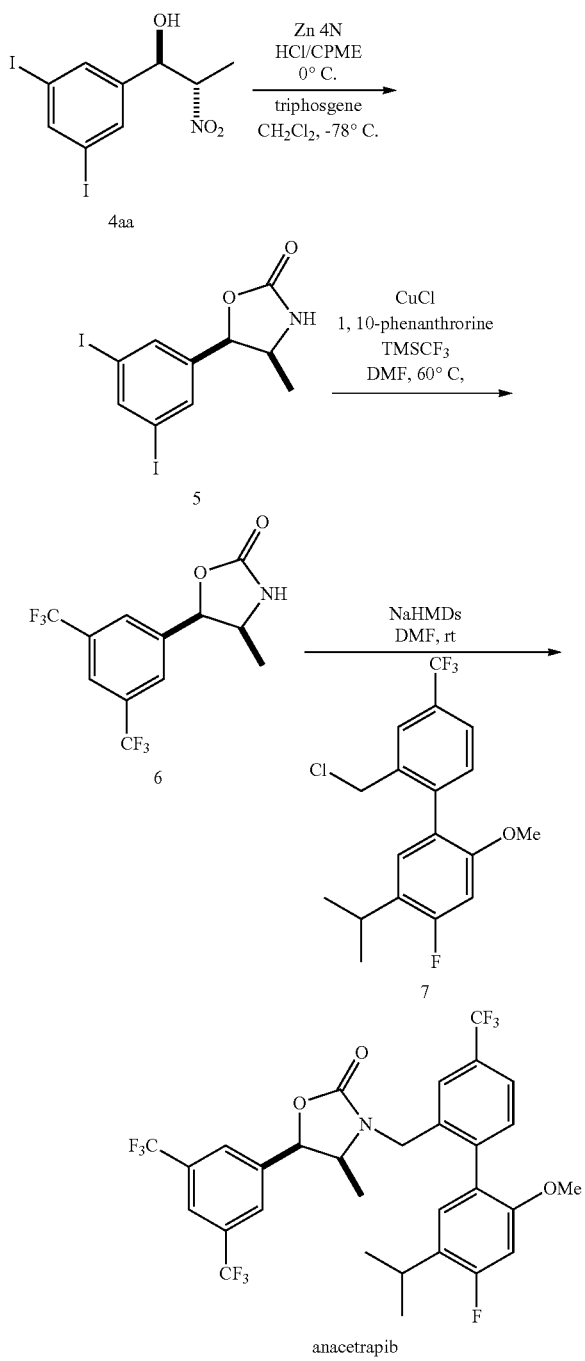

Compound 4aa (43 mg, 0.1 mmol) was dissolved in 4 N hydrochloric acid cyclopentyl methyl ether (CPME) solution (1.5 mL, 6 mmol), and the resultant solution was cooled to 0° C. Thereafter, zinc powder (196 mg, 3.0 mmol) was added thereto portionwise. The resultant mixture was stirred at 0° C. for 1 hour in an Ar atmosphere, and then aqueous sodium hydroxide solution (10% by mass) (3 mL) was added thereto, followed by stirring at room temperature for 30 minutes. The precipitates that formed were filtrated under reduced pressure through Celite, and the residue was washed with ethyl acetate (30 mL, three times) and water (10 mL). The organic layer of the filtrate was separated and the aqueous layer was extracted with ethyl acetate three times. The combined organic layer was washed with saturated brine and then dried with sodium sulfate anhydrate. After filtration and concentration, the residue was dissolved in methylene chloride (1 mL) and cooled to 0° C., and diisopropylethylamine (78 mg) and triphosgene (15 mg, 0.05 mmol) were added thereto. The resultant mixture was stirred at room temperature for 12 hours in an Ar atmosphere, and 1 N hydrochloric acid and ethyl acetate were added thereto. The organic layer was washed sequentially with water, a saturated aqueous sodium hydrogen carbonate solution, water and saturated brine, and then dried with sodium sulfate anhydrate. After filtration and concentration, the residue was purified through silica gel column chromatography (hexane: ethyl acetate=2:1 to 1:1 (v/v)) to thereby obtain the above Compound 5 as a white solid (30 mg, 70% yield, 2 steps).

(4S,5R)-5-(3,5-Diiodophenyl)-4-methyloxazolidin-2-one (Compound 5)

White Solid
mp: 113° C.-115° C.
IR (KBr): v1752, 1546, 1332, 1231, 1122 cm$^{-1}$
$^1$H NMR (CDCl$_3$): δ8.04 (dd, J=1.6, 1.4 Hz, 1H), 7.61 (dd, J=1.4, 0.5 Hz, 2H), 5.57 (d, J=7.8 Hz, 1H), 4.23-4.16 (m, 1H), 0.86 (d, J=6.6 Hz)
$^{13}$C NMR (CDCl$_3$): δ158.7, 145.3, 138.8, 134.1, 94.9, 78.9, 52.1, 17.8
ESI-MS m/z 452 [M+Na]$^+$
HRMS (ESI-TOF) calcd. for C$_{10}$H$_9$I$_2$NO$_2$Na m/z 451.8615 [M+Na]$^+$. found 451.8612.
[α]D$^{26}$ −68.7 (c 1.05, CHCl$_3$, 99% ee)

Synthesis of Compound 6

Copper(I) chloride (99 mg, 1.0 mmol), potassium-tert-butoxide (112 mg, 1.0 mmol) and 1,10-phenanthroline (180 mg, 1.0 mmol) were added to a 20 mL test tube, which had been dried in vacuum with heating, and dried in vacuum at room temperature for 5 minutes. The atmosphere of the test tube was changed to an Ar atmosphere, and then dry DMF was added thereto using a syringe and the resultant mixture was stirred at room temperature for 1 hour. (Trimethylsilyl)trifluorometane (TMSCF$_3$) (150 μL, 1.0 mmol) was added dropwise thereto using a syringe, and the resultant mixture was stirred at room temperature for 1 hour. Then, a DMF solution (0.5 mL) of Compound 5 (107 mg, 0.25 mmol) was added dropwise thereto using a syringe, and the resultant mixture was stirred at 50° C. for 18 hours. The mixture was left to cool to room temperature, and then ethyl acetate was added thereto to suspend the mixture. The resultant mixture was filtrated through Celite, and the residue was washed with ethyl acetate. The filtrate was washed sequentially with 1 N hydrochloric acid, a saturated aqueous sodium hydrogen carbonate solution, water and saturated brine, and then dried with sodium sulfate anhydrate. After filtration and concentration, the residue was purified through silica gel column chromatography (hexane:ethyl acetate=2:1 to 1:1 (v/v)) to thereby obtain the above Compound 6 as a white solid (61 mg, 78% yield).

This reaction was performed with reference to Hiroyuki Morimoto, et al., Angew. Chem. Int. Ed. 2011, 50, 3793-3798.

(4S,5R)-5-(3,5-Bis(trifluoromethyl)phenyl)-4-methyloxazolidin-2-one (Compound 6)

White Solid
mp: 123° C.-124° C.
IR (KBr): v1748, 1335, 1281, 1122 cm$^{-1}$
$^1$H NMR (CDCl$_3$): δ7.90 (s, 1H), 7.79 (s, 2H), 5.83 (d, J=7.8 Hz, 1H), 5.32 (brs, 1H), 4.31 (dq, J=7.8, 6.6 Hz, 1H), 0.84 (d, J=6.6 Hz, 3H)
$^{13}$C NMR (acetone-d$_6$): δ158.2, 140.8, 132.2 (q, JC-F=33.5 Hz), 127.7 (q, JC-F=3.8 Hz), 124.3 (q, JC-F=272 Hz), 122.9 (q, JC-F=3.8 Hz), 79.4, 52.2, 17.7
ESI-MS m/z 336 [M+Na]$^+$
HRMS (ESI-TOF) calcd. for C$_{12}$H$_9$F$_6$NO$_2$Na m/z 336.0430 [M+Na]$^+$. found 336.0431.
[α]D$^{25}$ −90.3 (c 0.72, CHCl$_3$, 99% ee)

<Synthesis of Compound 7>

Compound 7 presented in the above reaction scheme was synthesized according to Stephane G. Ouellet, et al., J. Org. Chem. 2011, 76, 1436-1439.

<Synthesis of Anacetrapib>

A dry DMF solution (0.6 mL) of Compound 6 (50 mg, 0.16 mmol) was cooled to −20° C. in an Ar atmosphere, and NaHMDS (1.0 M in THF: 190 μL, 0.19 mmol) was added dropwise thereto. The resultant mixture was stirred at room temperature for 1 hour, and then a dry DMF solution (0.5 mL) of Compound 7 (69 mg, 0.19 mmol) was added dropwise thereto using a syringe. The resultant mixture was stirred at room temperature for 18 hours, and then 1 N hydrochloric acid was added thereto and the mixture was extracted with ethyl acetate. The organic layer was washed sequentially with water, a saturated aqueous sodium hydrogen carbonate solution, water and saturated brine, and then dried with sodium sulfate anhydrate. After filtration and concentration, the residue was purified through silica gel column chromatography (hexane:ethyl acetate=20:1 to 5:1 (v/v)) to thereby obtain anacetrapib as a white solid (85 mg, 84% yield).

(4S,5R)-5-(3,5-Bis(trifluoromethyl)phenyl)-3-((4'-fluoro-5'-isopropyl-2'-methoxy-4-(trifluoromethyl)-[1,1'-biphenyl]-2-yl)methyl)-4-methyloxazolidin-2-one (anacetrapib)

White Solid
mp: 60-61° C.
IR (KBr): v1763, 1332, 1281, 1181, 1133 cm$^{-1}$
$^1$H NMR (C$_6$D$_6$, 1:1 mixture of atropisomers (two isomers can be observed through NMR because rotation of the C—C single bond at the biaryl is suppressed)): δ7.87 (s, 0.5H), 7.64 (s, 0.5H), 7.60 (s, 1H), 7.37 (d, J=8.2 Hz, 1H), 7.29 (d, J=6.9 Hz, 2H), 7.05-7.01 (m, 1H), 6.93 (d, J=8.5 Hz, 0.5H), 6.86 (d, J=8.4 Hz, 0.5H), 6.48 (d, J=11.9 Hz, 0.5H), 6.39 (d, J=11.9 Hz, 0.5H), 4.98 (d, J=15.8 Hz, 0.5H), 4.91 (d, J=15.6 Hz, 0.5H), 4.60 (d, J=7.8 Hz, 0.5H), 4.55 (d, J=7.6 Hz, 0.5H), 3.76 (d, J=15.6 Hz, 0.5H), 3.72 (d, J=15.8 Hz, 0.5H), 3.27-3.18 (m, 1H), 3.16 (s, 1.5H), 3.02 (s, 1.5H), 3.00-2.97 (m, 0.5H), 2.93-2.89 (m, 0.5H), 1.23-1.19 (m, 4.5H), 1.13 (d, J=6.9 Hz, 1.5H), −0.24 (d, J=5.0 Hz, 1.5H), −0.37 (d, J=5.0 Hz, 1.5H)
$^{13}$C NMR (acetone-d$_6$): δ163.1, 160.6, 157.3, 156.8, 156.5, 156.4, 156.3, 156.2, 143.1, 142.9, 140.4, 140.2, 137.9, 137.8, 132.9, 132.5, 132.2 (q, JC-F=33.5 Hz), 130.3 (q, JC-F=32.6 Hz), 130.1 (q, JC-F=32.6 Hz), 129.8, 129.8, 129.6, 129.5, 127.8, 127.8, 127.6, 127.5, 127.4, 125.8 (q, JC-F=3.8 Hz), 125.5 (q, JC-F=3.8 Hz), 125.2 (q, JC-F=271 Hz), 125.1 (q, JC-F=3.8 Hz), 124.6 (q, JC-F=2.9 Hz), 124.2 (q, JC-F=272 Hz), 123.0 (q, JC-F=3.8 Hz), 100.5, 100.3, 100.2, 100.1, 77.6, 77.5, 56.3, 56.2, 54.7, 54.6, 44.9, 43.8, 27.4, 27.3, 23.1, 23.0, 23.0, 22.9, 14.2, 14.1
ESI-MS m/z 660 [M+Na]$^+$
HRMS (ESI-TOF) calcd. for C$_{30}$H$_{26}$F$_{10}$NO$_3$ m/z 638.1748 [M+H]$^+$. found 638.1744.
[α]D$^{27}$ −8.3 (c 0.65, CHCl$_3$, 99% ee)

INDUSTRIAL APPLICABILITY

The catalyst of the present invention is capable of synthesizing an optically active anti-1,2-nitroalkanol compound with high anti-selectivity and very high enatiomeric excess and is further reusable, and thus it can be suitably used for a method for producing an optically active anti-1,2-nitroalkanol compound useful as a starting material of pharmaceutical products.

Aspects of the present invention are, for example, as follows.

<1> A catalyst, which is obtained by mixing a compound expressed by the following Structural Formula (1), a nitroalkane compound, a neodymium-containing compound, a sodium-containing compound, and a carbon structure:

Structural Formula (1)

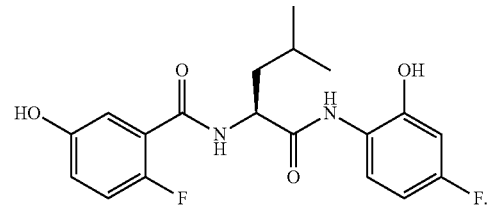

<2> The catalyst according to <1>, wherein the nitroalkane compound is a compound represented by the following General Formula (1):

$$R^1\text{—}CH_2\text{—}NO_2 \qquad \text{General Formula (1)}$$

where $R^1$ represents an alkyl group which has 1 to 20 carbon atoms and may have a substituent.

<3> The catalyst according to <1> or <2>, wherein the nitroalkane compound is nitroethane.

<4> The catalyst according to any one of <1> to <3>, wherein the carbon structure is carbon nanotube.

<5> The catalyst according to any one of <1> to <4>, wherein the neodymium-containing compound is Nd$_5$O (OCH(CH$_3$)$_2$)$_{13}$.

<6> The catalyst according to any one of <1> to <5>, wherein the sodium-containing compound is sodium bis(trimethylsilyl)amide.

<7> The catalyst according to any one of <1> to <6>, wherein the catalyst is obtained by: mixing the compound expressed by the Structural Formula (1), the neodymium-containing compound, the sodium-containing compound, and the carbon structure; and after the mixing, further mixing the nitroalkane compound.

<8> A method for producing an optically active anti-1,2-nitroalkanol compound, the method including:
allowing an aldehyde compound and a nitroalkane compound having 2 or more carbon atoms to react in the presence of the catalyst according to any one of <1> to <7>.

What is claimed is:
1. A method for producing a catalyst, which is obtained by first mixing a compound expressed by the following Struc- tural Formula (1), a neodymium-containing compound, a sodium-containing compound, and a carbon structure; and after the first mixing, further second mixing a nitroalkane compound:

Structural Formula (1)

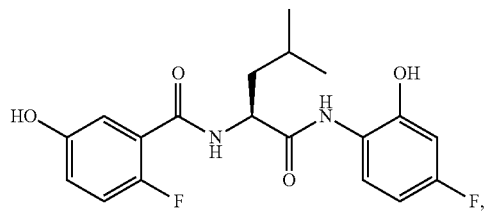

wherein the catalyst is a heterogeneous composite metallic complex, in which the compound expressed by the Structural Formula (1) is coordinated with neodymium and sodium; and wherein the first mixing is conducted in an absence of water.

2. The method for producing a catalyst according to claim 1, wherein the nitroalkane compound is a compound represented by the following General Formula (1):

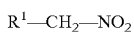    General Formula (1)

where $R^1$ represents an alkyl group which has 1 to 20 carbon atoms and may have a substituent.

3. The method for producing a catalyst according to claim 1, wherein the nitroalkane compound is nitroethane.

4. The method for producing a catalyst according to claim 1, wherein the carbon structure is carbon nanotube.

5. The method for producing a catalyst according to claim 1, wherein the neodymium-containing compound is $Nd_5O(OCH(CH_3)_2)_{13}$.

6. The method for producing a catalyst according to claim 1, wherein the sodium-containing compound is sodium bis(trimethylsilyl)amide.

7. A method for producing an optically active anti-1,2-nitroalkanol compound, the method comprising:

allowing an aldehyde compound and a nitroalkane compound having 2 or more carbon atoms to react in the presence of a catalyst to obtain the optically active anti-1,2-nitroalkanol compound, wherein the catalyst is obtained by first mixing a compound expressed by the following Structural Formula (1), a nitroalkane compound, a neodymium-containing compound, a sodium-containing compound, and a carbon structure; and after the first mixing, further second mixing a nitroalkane compound:

Structural Formula (1)

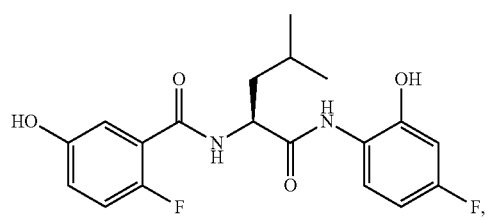

wherein the catalyst is a heterogeneous composite metallic complex, in which the compound expressed by the Structural Formula (1) is coordinated with neodymium and sodium; and wherein the first mixing is conducted in an absence of water.

8. The method according to claim 7, wherein the nitroalkane compound is a compound represented by the following General Formula (1):

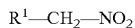    General Formula (1)

where $R^1$ represents an alkyl group which has 1 to 20 carbon atoms and may have a substituent.

9. The method according to claim 7, wherein the nitroalkane compound is nitroethane.

10. The method according to claim 7, wherein the carbon structure is carbon nanotube.

11. The method according to claim 7, wherein the neodymium-containing compound is $Nd_5O(OCH(CH_3)_2)_{13}$.

12. The method according to claim 7, wherein the sodium-containing compound is sodium bis(trimethylsilyl)amide.

* * * * *